(12) United States Patent
Greep et al.

(10) Patent No.: US 11,039,876 B2
(45) Date of Patent: Jun. 22, 2021

(54) HAND-HELD INSTRUMENT WITH EXTENDABLE SHAFT LOCKING MECHANISM

(71) Applicant: Megadyne Medical Products, Inc., Draper, UT (US)

(72) Inventors: Darcy W. Greep, Herriman, UT (US); Chad S. Frampton, American Fork, UT (US)

(73) Assignee: Megadyne Medical Products, Inc., Draper, UT (US)

( * ) Notice: Subject to any disclaimer, the term of this patent is extended or adjusted under 35 U.S.C. 154(b) by 269 days.

(21) Appl. No.: 15/596,266

(22) Filed: May 16, 2017

(65) Prior Publication Data

US 2018/0333193 A1    Nov. 22, 2018

(51) Int. Cl.
 *A61B 18/14*  (2006.01)
 *A61B 17/00*  (2006.01)
 (Continued)

(52) U.S. Cl.
 CPC ........ *A61B 18/1402* (2013.01); *A61B 18/148* (2013.01); *A61B 18/16* (2013.01);
 (Continued)

(58) Field of Classification Search
 CPC .......... A61B 18/1402; A61B 2080/034; A61B 2018/00958; A61B 2018/1475;
 (Continued)

(56) References Cited

U.S. PATENT DOCUMENTS 4,657,016 A * 4/1987 Garito ................ A61B 17/3213
                                                         439/784
4,683,884 A    8/1987 Hatfield
(Continued)

FOREIGN PATENT DOCUMENTS

KR    10-2010-0044616 A    4/2010
WO         2012155922        11/2012

OTHER PUBLICATIONS

Non-Final Office Action received for U.S. Appl. No. 15/975,552, dated Sep. 18, 2020, 24 pages.
(Continued)

*Primary Examiner* — Jaymi E Della
*Assistant Examiner* — Sean W Collins
(74) *Attorney, Agent, or Firm* — Workman Nydegger

(57) ABSTRACT

An instrument includes a body having an interior conduit. A shaft extends distally out of the body and is movable between a retracted position and an extended position. A locking mechanism that selectively secures the shaft in the retracted and extended positions includes grooves in the body and a locking nut having pins that travel through the grooves to move the locking nut between a locked position and an unlocked position. The locking mechanism also includes compression flanges that flex towards and apply pressure/friction to the shaft when the locking nut is in the locked position and release/reduce the pressure/friction from the shaft when the locking nut is in the unlocked position. The compression flanges restrict the movement of the shaft when the compression flanges are flexed towards, and apply pressure to the shaft.

20 Claims, 11 Drawing Sheets

(51) Int. Cl.
  *A61B 18/00* (2006.01)
  *A61B 90/00* (2016.01)
  *A61B 18/12* (2006.01)
  *A61B 18/16* (2006.01)

(52) U.S. Cl.
  CPC .............. *A61B 2017/00991* (2013.01); *A61B 2018/00589* (2013.01); *A61B 2018/00595* (2013.01); *A61B 2018/00601* (2013.01); *A61B 2018/00607* (2013.01); *A61B 2018/00702* (2013.01); *A61B 2018/00958* (2013.01); *A61B 2018/1253* (2013.01); *A61B 2018/1412* (2013.01); *A61B 2090/034* (2016.02); *A61B 2218/007* (2013.01); *A61B 2218/008* (2013.01)

(58) Field of Classification Search
  CPC .... A61B 2218/008; A61B 2018/00053; A61B 2018/00172; A61B 2017/00982; A61B 2017/00991; A61B 8/445; A61B 1/00066; A61B 1/00105; A61B 1/00112; A61B 1/00121
  See application file for complete search history.

(56) References Cited

U.S. PATENT DOCUMENTS

| | | |
|---|---|---|
| 5,181,916 A | 1/1993 | Reynolds |
| 5,192,267 A | 3/1993 | Shapira |
| 5,195,959 A | 3/1993 | Smith |
| 5,244,462 A | 9/1993 | Delahuerga |
| 5,318,565 A | 6/1994 | Kuriloff |
| 5,431,650 A | 7/1995 | Cosmescu |
| 5,451,223 A | 9/1995 | Ben-Simhon |
| 5,460,602 A | 10/1995 | Shapira |
| 5,662,647 A | 9/1997 | Crow |
| 5,674,219 A | 10/1997 | Monson |
| 5,693,044 A | 12/1997 | Cosmescu |
| 5,830,214 A | 11/1998 | Flom |
| 5,888,200 A | 3/1999 | Walen |
| 6,117,134 A | 9/2000 | Cunningham |
| 6,146,353 A | 11/2000 | Platt |
| 6,231,571 B1 | 5/2001 | Ellman |
| 6,293,945 B1 | 9/2001 | Parins |
| 6,355,034 B2 | 3/2002 | Cosmescu |
| 6,379,350 B1 | 4/2002 | Sharkey |
| 6,391,027 B1 | 5/2002 | Farin |
| 6,530,924 B1 | 3/2003 | Ellman |
| 6,635,034 B1 | 10/2003 | Cosmescu |
| 6,663,628 B2 * | 12/2003 | Peters .............. A61B 17/32002 606/170 |
| 6,702,812 B2 | 3/2004 | Cosmescu |
| 6,716,211 B2 | 4/2004 | Mulier |
| 6,802,842 B2 | 10/2004 | Ellman |
| 7,004,939 B2 | 2/2006 | Mackay |
| 7,083,601 B1 | 8/2006 | Cosmescu |
| 7,112,199 B2 | 9/2006 | Cosmescu |
| 7,198,626 B2 | 4/2007 | Lee |
| 7,241,294 B2 | 7/2007 | Reschke |
| 7,261,711 B2 | 8/2007 | Mulier |
| 7,329,253 B2 | 2/2008 | Brounstein |
| 7,387,625 B2 | 6/2008 | Hovda |
| 7,393,351 B2 | 7/2008 | Woloszko |
| 7,419,488 B2 | 9/2008 | Ciarrocca |
| 7,435,247 B2 | 10/2008 | Woloszko |
| 7,491,200 B2 | 2/2009 | Underwood |
| 7,494,473 B2 | 2/2009 | Eggers |
| 7,717,912 B2 | 5/2010 | Woloszko |
| 7,824,398 B2 | 11/2010 | Woloszko |
| 7,828,797 B2 | 11/2010 | Eggers |
| 7,935,109 B2 | 5/2011 | Cosmescu |
| 7,988,689 B2 | 8/2011 | Woloszko |
| 8,002,732 B2 | 8/2011 | Visconti |
| 8,057,470 B2 | 11/2011 | Lee |
| 8,137,345 B2 | 3/2012 | McNall |
| 8,187,272 B2 | 5/2012 | Sensenbrenner |
| 8,241,278 B2 | 8/2012 | Sartor |
| D669,581 S | 10/2012 | Van Wyk |
| 8,317,786 B2 | 11/2012 | Dahla |
| 8,323,279 B2 | 12/2012 | Dahla |
| 8,460,289 B2 | 6/2013 | Sartor |
| 8,518,018 B2 | 8/2013 | Minskoff |
| 2001/0018586 A1 | 8/2001 | Cosmescu |
| 2001/0051804 A1 | 12/2001 | Mulier |
| 2002/0013582 A1 | 1/2002 | Mulier |
| 2002/0049438 A1 | 4/2002 | Sharkey |
| 2002/0058938 A1 | 5/2002 | Cosmescu |
| 2002/0103485 A1 | 8/2002 | Melnyk |
| 2003/0135208 A1 | 7/2003 | Luigi |
| 2003/0181904 A1 | 9/2003 | Levine |
| 2004/0038584 A1 * | 2/2004 | Zahlit .................. H01R 24/40 439/489 |
| 2004/0049183 A1 | 3/2004 | Ellman |
| 2004/0162553 A1 | 8/2004 | Peng |
| 2004/0172009 A1 | 9/2004 | Marisi |
| 2005/0107782 A1 | 5/2005 | Reschke |
| 2005/0113825 A1 | 5/2005 | Cosmescu |
| 2005/0124986 A1 | 6/2005 | Brounstein |
| 2006/0218752 A1 * | 10/2006 | Potempa ............. B05C 17/0205 16/429 |
| 2006/0264928 A1 | 11/2006 | Kornerup |
| 2006/0276783 A1 | 12/2006 | Cosmescu |
| 2007/0209486 A1 | 9/2007 | Gauthier et al. |
| 2007/0265615 A1 | 11/2007 | Ben-Simhon |
| 2007/0289650 A1 | 12/2007 | Krywitsky |
| 2008/0103431 A1 | 5/2008 | Brounstein |
| 2009/0062791 A1 | 3/2009 | Lee |
| 2009/0069802 A1 | 3/2009 | Garito |
| 2010/0094283 A1 | 4/2010 | Cosmescu |
| 2010/0174283 A1 | 7/2010 | McNall |
| 2011/0077645 A1 | 3/2011 | Lin |
| 2011/0190768 A1 | 8/2011 | Shvetsov |
| 2012/0101497 A1 | 4/2012 | Jayaraj |
| 2012/0143186 A1 | 6/2012 | McNall |
| 2012/0203223 A1 | 8/2012 | Terry |
| 2012/0283718 A1 | 11/2012 | Cosmescu |
| 2012/0283728 A1 | 11/2012 | Cosmescu |
| 2013/0006236 A1 | 1/2013 | Greep |
| 2013/0110108 A1 | 5/2013 | Davison |
| 2013/0204246 A1 | 8/2013 | Greep |
| 2014/0276763 A1 * | 9/2014 | Greep .................... A61C 1/052 606/34 |
| 2015/0123398 A1 * | 5/2015 | Sanders .............. F16L 37/0841 285/330 |
| 2015/0126971 A1 | 5/2015 | Muller |
| 2015/0180167 A1 * | 6/2015 | Haas .................... H01R 13/64 439/311 |
| 2016/0143662 A1 | 5/2016 | Mulier |
| 2017/0049510 A1 | 2/2017 | Zinnanti |
| 2018/0333191 A1 | 11/2018 | Frampton et al. |
| 2020/0155231 A1 | 5/2020 | Greep et al. |

OTHER PUBLICATIONS

Final Office Action received for U.S. Appl. No. 15/975,552, dated Feb. 24, 2021, 21 pages.

* cited by examiner

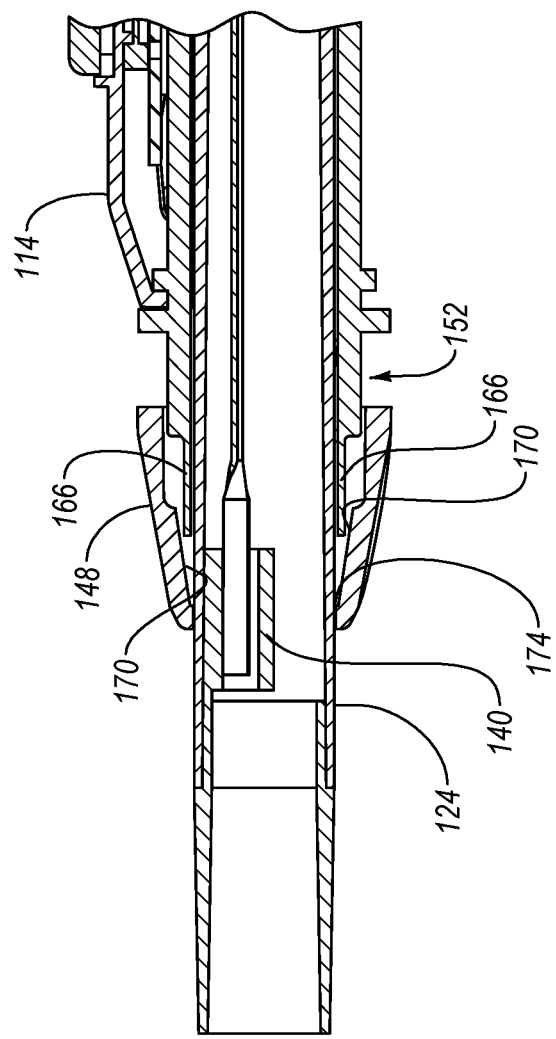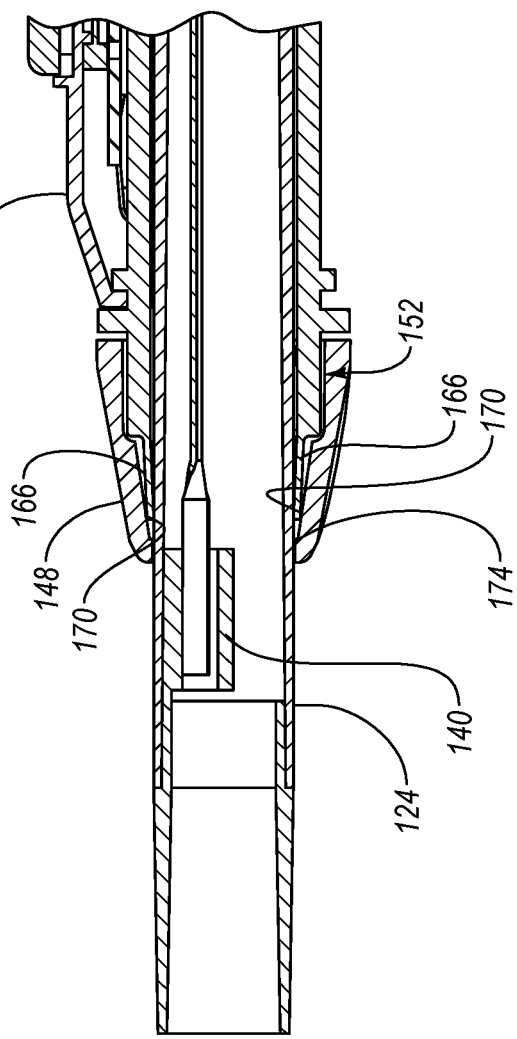

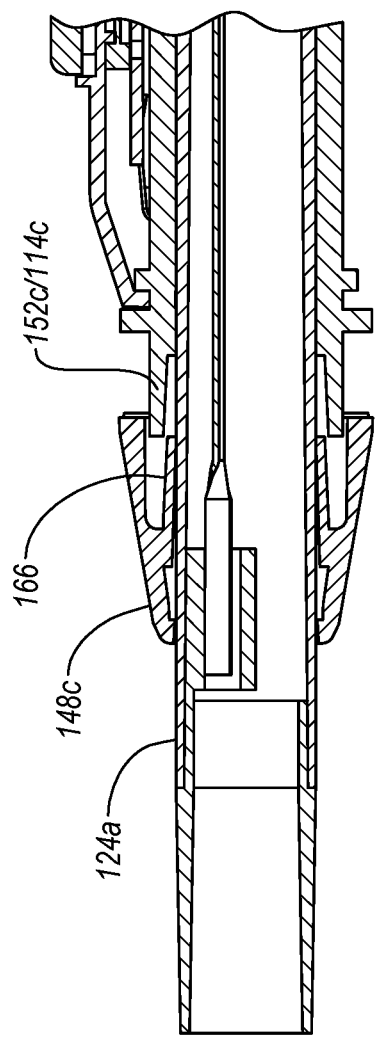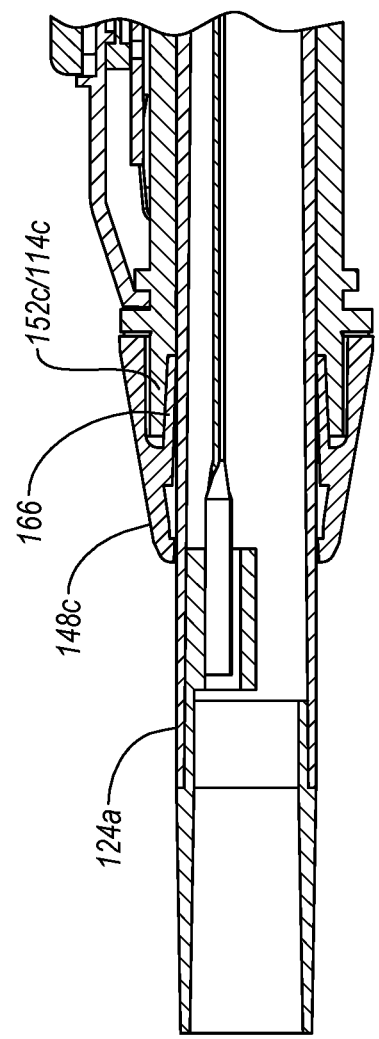

ated shafts. More particularly, the disclosure relates to locking mechanisms for locking extendable shafts to instruments and in various positions relative to such instruments.

HAND-HELD INSTRUMENT WITH EXTENDABLE SHAFT LOCKING MECHANISM

BACKGROUND

1. Technical Field

This disclosure relates to instruments with extendable shafts. More particularly, the disclosure relates to locking mechanisms for locking extendable shafts to instruments and in various positions relative to such instruments.

2. The Relevant Technology

As is known to those skilled in the art, modern surgical techniques typically employ radio frequency (RF) power to cut tissue and coagulate bleeding encountered in performing surgical procedures. Electrosurgery is widely used and offers many advantages including the use of a single surgical instrument for both cutting and coagulation. A monopolar electrosurgical system has an active electrode, such as in the form of an electrosurgical instrument having a hand piece and a conductive electrode or tip, which is applied by the surgeon to the patient at the surgical site to perform surgery and a return electrode to connect the patient back to the generator.

The electrode or tip of the electrosurgical instrument is small at the point of contact with the patient to produce an RF current with a high current density in order to produce a surgical effect of cutting or coagulating tissue. The return electrode carries the same RF current provided to the electrode or tip of the electrosurgical instrument, thus providing a path back to the electrosurgical generator.

When an electrosurgical instrument is used for cutting or coagulation, smoke is commonly produced. A surgeon or assistant often uses a separate smoke evacuation device to remove the smoke from the surgical field. Smoke evacuation devices commonly include a suction wand connected to a vacuum device via tubing. The surgeon or assistant holds the suction wand close to the surgical site and the smoke is drawn into the suction wand and through the tubing. However, using a smoke evacuation device separate from the electrosurgical instrument is not ideal. Using a separate smoke evacuation device requires additional hands and instruments near the surgical site, which can obscure the surgeon's view of the surgical site and reduce the room available around the surgical site for the surgeon to move.

As a result, combination electrosurgical instrument and smoke evacuation devices have been developed. These combination devices often include a hand piece that can receive an electrode or tip in a distal end thereof for performing electrosurgical procedures. The hand piece is connected to a generator via a power cable to convey RF current to the electrode or tip. Additionally, a smoke evacuation hose is connected between the hand piece and a vacuum to draw smoke away from the surgical site.

Some combination electrosurgical instrument and smoke evacuation devices include an extendable shaft. The electrode or tip can be mounted in the distal end of the shaft, and the shaft can be extended from the hand piece to increase the reach of the device. The extendable shaft may also include an open distal end and conduit therethrough to facilitate the evacuation of smoke through the shaft and the hand piece.

Some previous combination devices with extendable shafts include a locking feature for securing the extendable shaft in various extended positions. Such devices and features have various shortcomings. For instance, when the locking feature is loosened or in an unlocked configuration, the extendable shaft can be freely removed from the hand piece. As a result, the device has to be reassembled in order for the device to function properly. In some instances, such as during a surgical procedure, having to reassemble the device can create delays and pose safety risks to the patient. Furthermore, a surgeon or other operating room personnel may not know how to properly reassemble the device. Moreover, attempts to reassemble the device may result in damage to the device which can render the device inoperable.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

Figure 13:
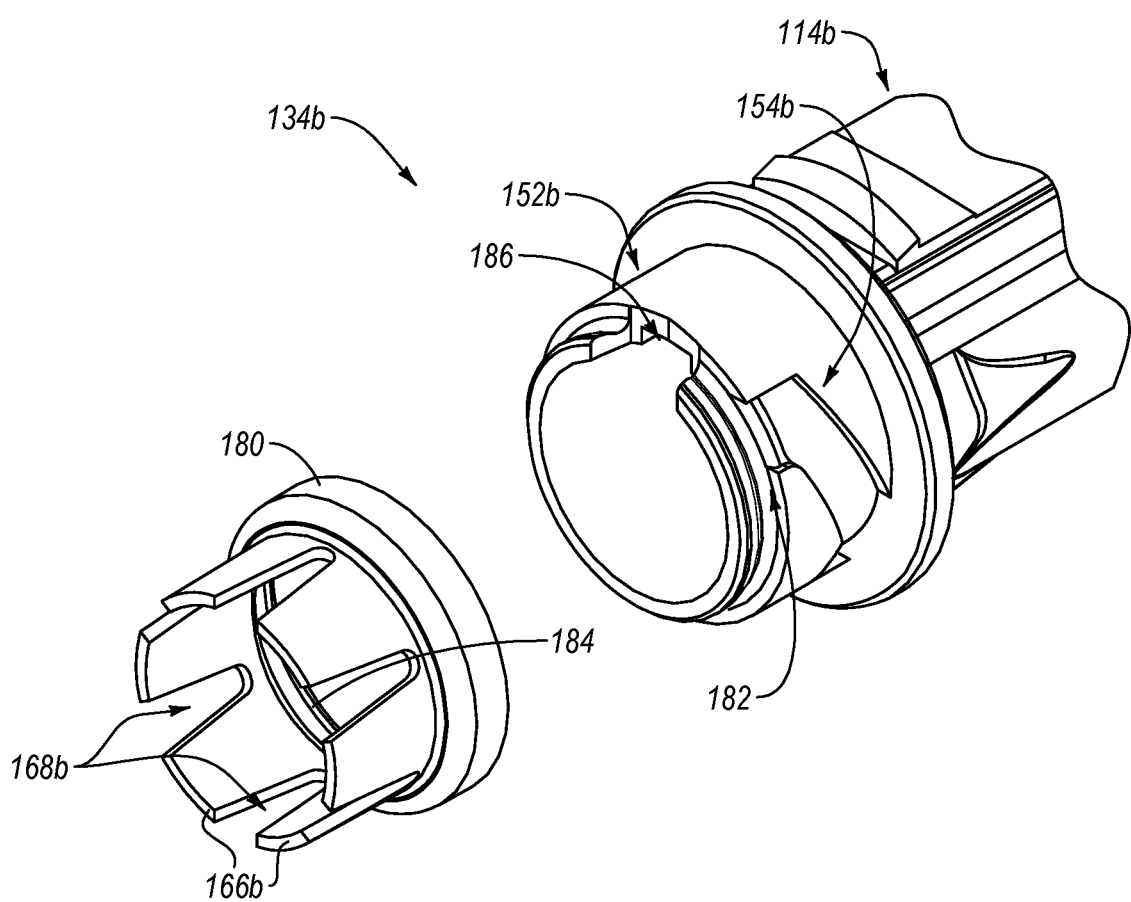
Figure 14:
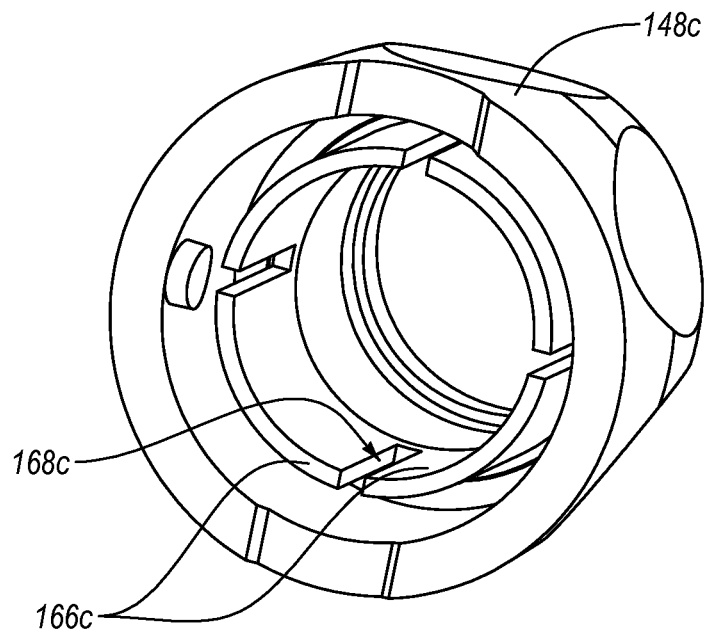
Figure 15:
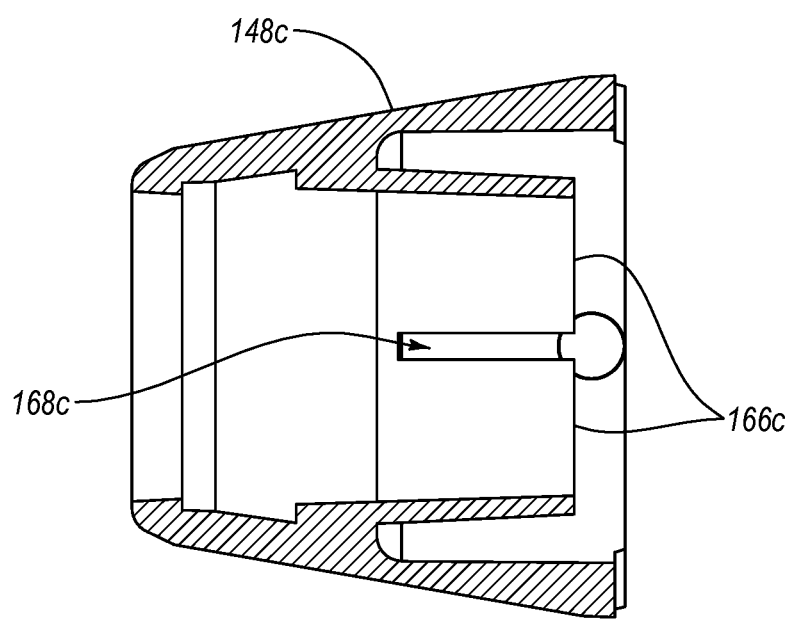

10B illustrates a partial cross-sectional view of another embodiment of a locking mechanism showing the interior of a locking nut;

FIG. 11 illustrates a cross-sectional view of the locking mechanism of FIGS. 7-10A in an unlocked position;

FIG. 12 illustrates a cross-sectional view of the locking mechanism of FIGS. 7-10A in a locked position;

FIG. 13 illustrates a partially exploded view a portion of a locking mechanism according to another embodiment;

FIG. 14 illustrates a perspective view of a locking nut according to an example embodiment;

FIG. 15 illustrates a cross-sectional view of the locking nut of FIG. 14;

FIG. 16 illustrates a cross-sectional view of a locking mechanism incorporating the locking nut of FIGS. 14-15 in an unlocked position; and FIG. 17 illustrates a cross-sectional view of a locking mechanism incorporating the locking nut of FIGS. 14-15 in a locked position.

DETAILED DESCRIPTION

The present disclosure relates to locking mechanisms for securing an extendable shaft to an instrument and in various positions relative to the instrument. In some embodiments, the instrument is a hand-held instrument, such as an electrosurgical instrument. In other embodiments, the instrument may not include a hand piece or otherwise be specifically designed as a hand-held instrument. Rather, the instrument may include a body, an extendable shaft, and a locking mechanism as disclosed herein.

In some embodiments, the extendable shaft may provide functionality to an implement disposed at the distal end of the shaft. For instance, an electrode tip may be disposed at the distal end of the extendable shaft and electrical current may be communicated to the electrode tip via or through the extendable shaft.

In some embodiments, the extendable shaft may provide for the evacuation or delivery of fluid therethrough. For instance, the extendable shaft may have a conduit extending therethrough, through which smoke or other fluids may be evacuated away from a surgical site. The conduit may also be used to deliver fluid to a surgical site.

Reference is made herein to the evacuation of smoke and components that facilitate such function. It will be appreciated that references to "smoke" is merely for simplicity and convenience, and is not intended to limit the disclosed and claimed embodiments to evacuation of only smoke. Rather, the disclosed and claimed embodiments may be used to evacuate substantially any type of fluid, including liquids, gases, vapors, smoke, or combinations thereof. Additionally, rather than simply evacuating fluid, it is contemplated that at least some of the embodiments may be used to deliver fluids to a desired location, such as a surgical site. Still further, while the illustrated embodiments include smoke evacuation features and capabilities, it will be appreciated that other embodiments of the present disclosure may not include smoke evacuation features or capabilities.

Figure 1:
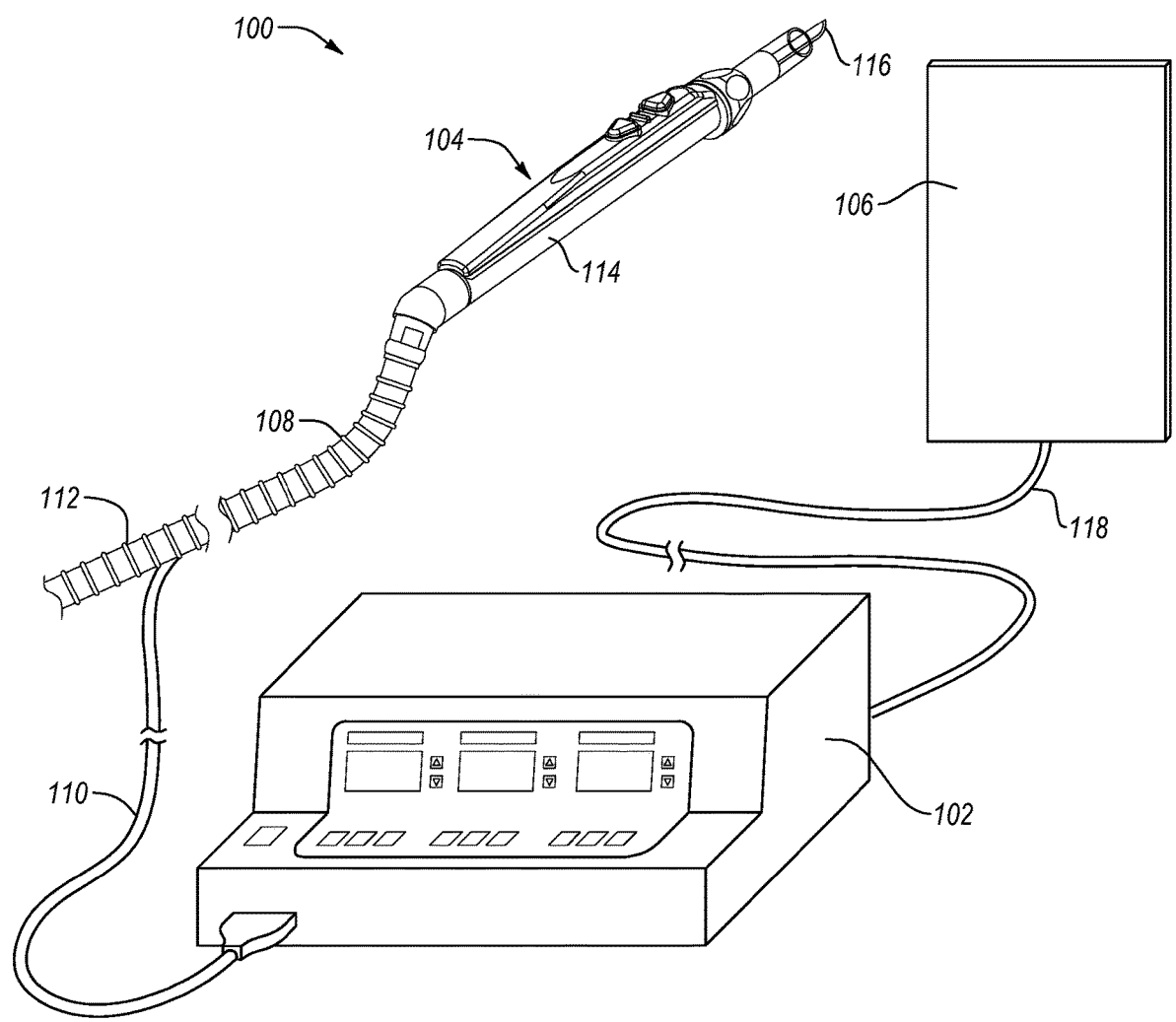
FIG. 1 illustrates an exemplary electrosurgical system.

FIG. 1 illustrates an exemplary electrosurgical system 100. The illustrated embodiment includes a signal generator 102, an electrosurgical instrument 104, and a return electrode 106. Generator 102, in one embodiment, is an RF wave generator that produces RF electrical energy. Connected to electrosurgical instrument 104 is a utility conduit 108. In the illustrated embodiment, utility conduit 108 includes a cable 110 that communicates electrical energy from generator 102 to electrosurgical instrument 104. The illustrated utility conduit 108 also includes a vacuum hose 112 that conveys captured/collected smoke and/or fluid away from a surgical site. In some embodiments, such as that illustrated in FIG. 1, cable 110 can extend through at least a portion of vacuum hose 112.

Generally, electrosurgical instrument 104 includes a hand piece 114 and an electrode tip 116. Electrosurgical instrument 104 communicates electrical energy to a target tissue of a patient to cut the tissue and/or cauterize blood vessels within and/or near the target tissue. Specifically, an electrical discharge is delivered from electrode tip 116 to the patient in order to cause heating of cellular matter of the patient that is in close contact with or proximity to electrode tip 116. The heating takes place at an appropriately high temperature to allow electrosurgical instrument 104 to be used to perform electrosurgery. Return electrode 106 is connected to generator 102 by a cable 118 in order to complete the circuit and provide a return electrical path to wave generator 102 for energy that passes into the patient's body.

Figure 2:
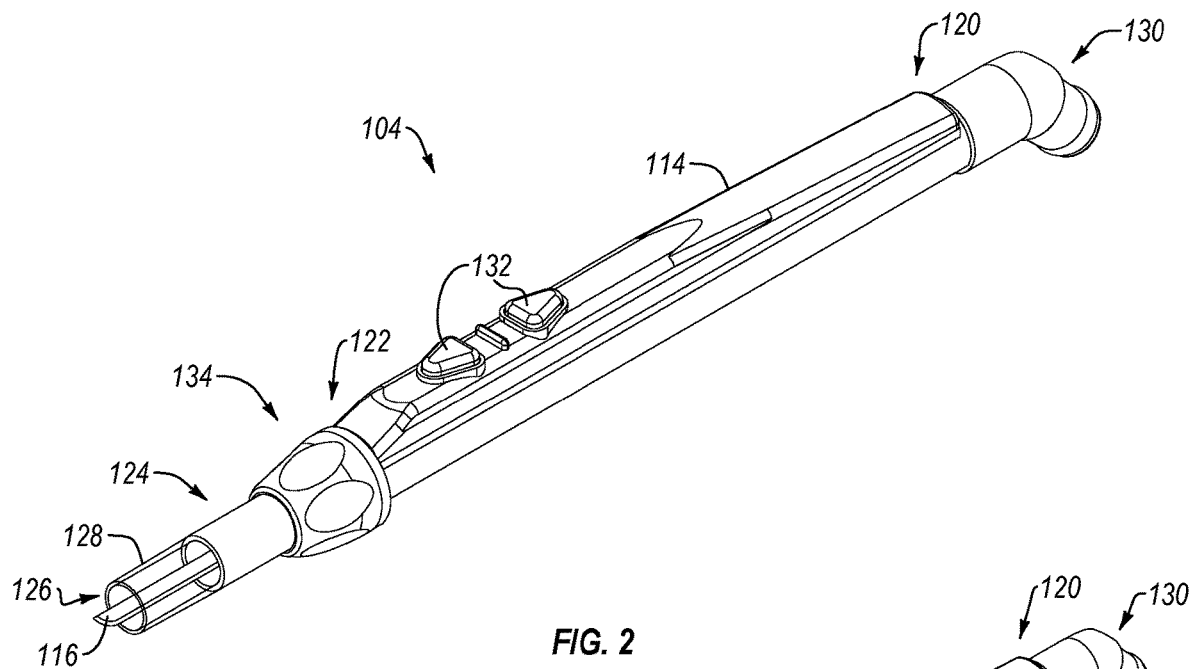
FIG. 2 illustrates an electrosurgical instrument of the system of FIG. 1 with an extendable shaft in a retracted configuration.
Figure 3:
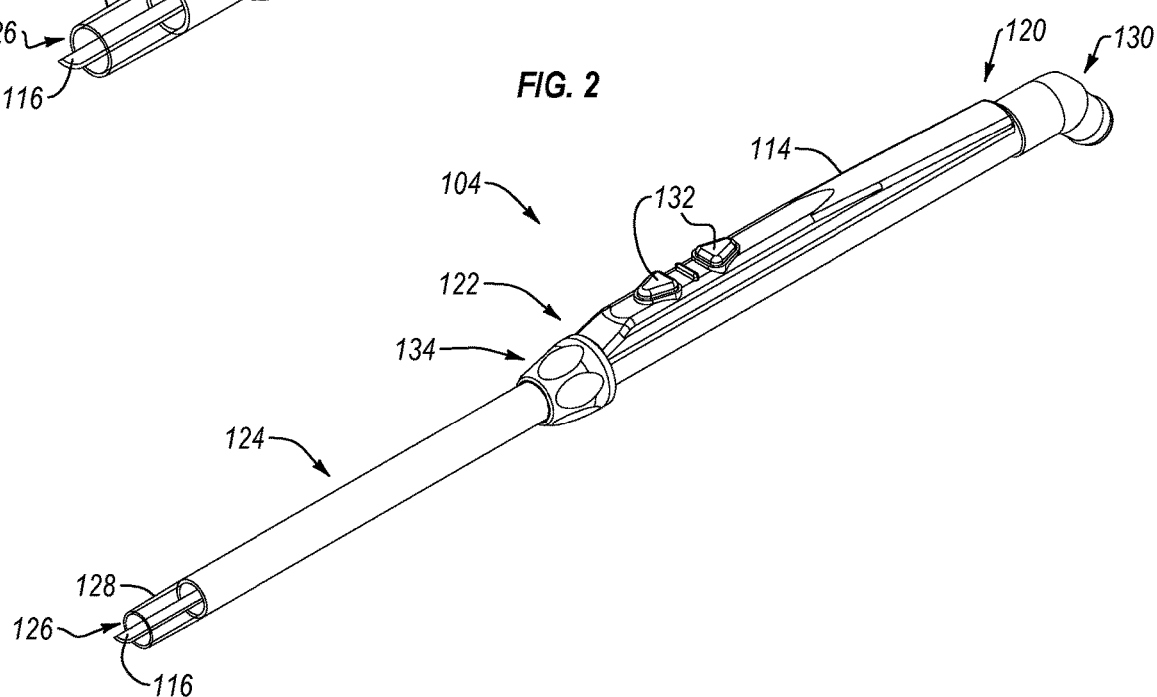
FIG. 3 illustrates the electrosurgical instrument of FIG. 2 with the extendable shaft in an extended configuration.

FIGS. 2 and 3 illustrate perspective views of electrosurgical instrument 104 separate from the rest of system 100. Hand piece 114 of electrosurgical instrument 104 has a proximal end 120 and a distal end 122. An extendable shaft 124 is selectively extendable from and retractable into (e.g., translatable along an axis running in the proximal/distal direction) distal end 122. FIG. 2 illustrates extendable shaft 124 in a retracted position where a substantial portion of extendable shaft 124 is disposed within hand piece 114. Nevertheless, as can be seen in FIG. 2, a portion of extendable shaft 124 can extend out of hand piece 114 even when shaft 124 is in the retracted position.

In contrast, FIG. 3 illustrates extendable shaft 124 in an extended position where a substantial portion of extendable shaft 124 is extended from or disposed outside of hand piece 114. Even when shaft 124 is in the extended position, a portion of shaft 124 remains disposed within hand piece 114 so that shaft 124 and hand piece 104 remain connected to one another.

Although not illustrated, extendable shaft 124 can also be extended from hand piece 114 to various intermediate extended positions between the extended and retracted positions shown in FIGS. 2 and 3. In some embodiments, extendable shaft 124 can be extended to one or more discreet intermediate extended positions. In such embodiments, extendable shaft 124 and hand piece 114 may include cooperating features (e.g., recesses, protrusions, etc.) that facilitate location of extendable shaft in the one or more discreet intermediate extended positions. In other embodiments, the one or more intermediate positions may not be discreet positions. Rather, extendable shaft 124 can be extended to substantially any position between the extended and retracted positions shown in FIGS. 2 and 3.

Extendable shaft 124 can also include a channel or conduit 126 extending therethrough. As discussed elsewhere herein, conduit 126 can be used to convey fluids through instrument 104. For example, smoke or other fluids at a surgical site can be evacuated through conduit 126. In other embodiments, fluids (e.g., water, saline, etc.) may be delivered to a target site through conduit 126.

In the illustrated embodiment, electrode tip 116 is received partially within the distal end of the extendable shaft 124. A portion of electrode tip 116 extends from the distal end of shaft 124 so as to be able to interact with patient tissue during an electrosurgical procedure. As can be seen in FIGS. 2 and 3, electrode tip 116 is mounted within the distal end of shaft 124 such that electrode tip 116 moves with shaft 124 as shaft 124 is moved between the retracted and extended positions.

In some embodiments, such as that shown in FIGS. 2 and 3, the distal end of shaft 124 may be transparent or semi-transparent. For instance, the distal end of shaft 124 may comprise a nozzle 128 formed of a transparent or semi-transparent material. In other embodiments, more than just the distal end of shaft 124 can be transparent or semi-transparent. Making at least the distal end of shaft 124 transparent or semi-transparent can provide a surgeon with an increased field of view when using instrument 104. For instance, the transparent or semi-transparent portion of shaft 124 may allow a surgeon to see the portion of the surgical field on the opposite side of the shaft 124 without requiring the surgeon to move the instrument 104.

As illustrated in FIGS. 2 and 3, hand piece 114 includes a receptacle 130 at proximal end 120. Alternative embodiments can include a receptacle on a top and/or side section of a hand piece and/or at different locations along the length of the hand piece (i.e., between the proximal and distal ends thereof). Receptacle 130 can be configured to have utility conduit 108 (or vacuum hose 112 thereof) (FIG. 1) connected thereto. Receptacle 130 can also be configured to have cable 110 (FIG. 1) extend therethrough. In some embodiments, including the illustrated embodiment, receptacle 130 can have an angled configuration. In other embodiments, receptacle 130 can have a straight configuration. Furthermore, in some embodiments, receptacle 130 can be connected to hand piece 114 in a fixed manner. In other embodiments, receptacle 130 can be rotatably or pivotally connected to hand piece 114 such that hand piece 114 can rotate or pivot relative to receptacle 130 and utility conduit 108 or vice versa.

Regardless of the specific configuration of receptacle 130, utility conduit 108 (or cable 110 or vacuum hose 112 thereof) can be connected to instrument 104 to provide instrument 104 with certain capabilities or functionality. As noted above, for instance, cable 110 can communicate electrical energy from generator 102 to instrument 104. The electrical energy can be communicated through instrument 104 to electrode tip 116 during an electrosurgical procedure. When vacuum hose 112 is connected to instrument 104, instrument 104 can be used to evacuate smoke/fluid away from a surgical site through conduit 126, hand piece 114, and vacuum hose 112.

The operation of instrument 104 can be controlled at least partially with one or more controls 132 on hand piece 114. The one or more controls 132 enable a user to adjust one or more parameters of the instrument 104, such as increasing or decreasing electrical power delivery through the instrument, turning the instrument on and off, adjusting the instrument for different operating modes (cut, coagulate, cut-coagulate blend), activating a vacuum, etc. For example, the controls 132 can provide a connection for transmitting control signals from the instrument 104 to generator 102 and/or a vacuum unit.

Instrument 104 also includes a locking mechanism 134. As will be discussed in greater detail below, locking mechanism 134 can be used to selectively secure shaft 124 is a desired position relative to hand piece 114. Additionally, locking mechanism 134 can also be selectively loosened to allow shaft 124 to be repositioned relative to hand piece 114. Furthermore, locking mechanism 134 can also secure shaft 124 to hand piece 114 such that shaft 124 cannot be inadvertently removed entirely from hand piece 114.

Figure 4:
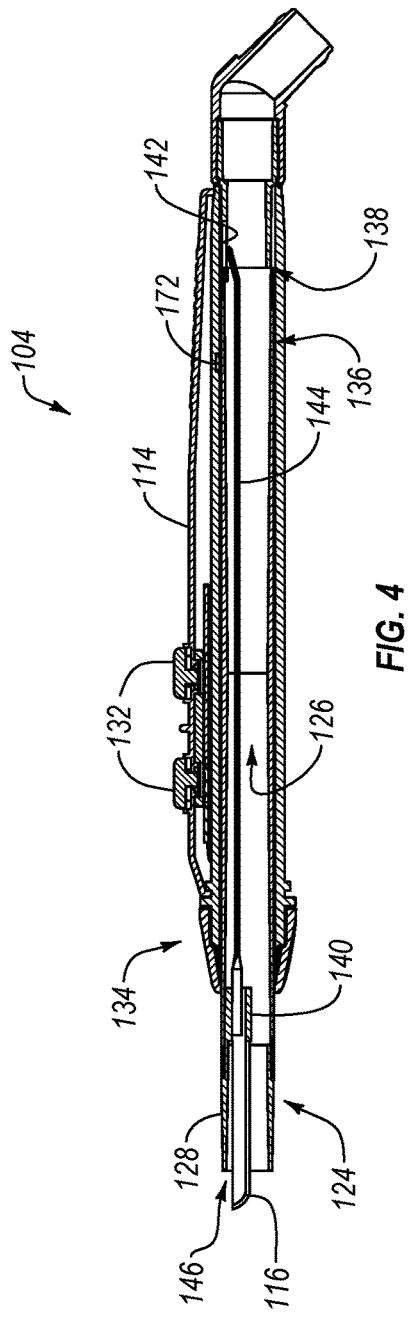
FIG. 4 illustrates a cross-sectional view of the electrosurgical instrument of FIGS. 2 and 3, showing the extendable shaft in the retracted configuration.

Attention is now directed to FIG. 4, which illustrates a cross-sectional view of instrument 104. FIG. 4 illustrates the extendable shaft 124 in a retracted position, showing that much of the extendable shaft 124 can be positioned within an interior chamber or conduit 136 of hand piece 114. In the illustrated embodiment, interior conduit 136 is configured in size and shape to enclose extendable shaft 124 (e.g., at least the portions not extending distally beyond hand piece 114) so that extendable shaft 124 fits within interior conduit 136 and is selectively translatable within interior conduit 136. As shown, interior conduit 136 is in fluid communication with the atmosphere exterior to hand piece 114 via conduit 126 in shaft 124, enabling the capture of smoke into interior conduit 136 through conduit 126.

In some embodiments, instrument 104 includes a back stop 138 positioned to limit proximal translation of extendable section 124 within interior conduit 136. For example, back stop 138 can be disposed at a position such that when extendable shaft 124 is fully retracted, at least nozzle 128 and/or electrode tip 116 is at or near the distal portion of hand piece 114 but not retracted into the interior of the hand piece 114.

The illustrated back stop 138 is formed as part of receptacle 130 to prevent proximal movement of extendable shaft 124 past back stop 138. Alternatively, back stop 138 can be formed as a crossbar, wall, rib, detent, abutment, catch, brace, and/or other mechanisms of limiting proximal movement of shaft 124.

In the illustrated embodiment, shaft 124 includes a collet 140 disposed therein near the distal end of shaft 124. Collet 140 is configured to have a portion (e.g., a shaft or shank) of electrode tip 116 mounted therein. With electrode tip 116 mounted in collet 140, a portion of electrode tip 116 extends distally from shaft 124 as shown so that electrode tip 116 can interact with patient tissue.

In some embodiments, such as the illustrated embodiment, collet 140 and/or electrode tip 116 are electrically connected to hand piece 114 by way of a sliding electrical connection. More specifically, hand piece 114 includes a conductor 142 disposed on an interior surface of interior conduit 136. Similarly, extendable shaft 124 includes a sliding conductor 144. Sliding conductor 144 is in electrical contact with conductor 142 and collet 140 and/or electrode tip 116.

Conductor 142 is electrically connected to cable 110 (FIG. 1). Accordingly, electrical energy communicated to instrument 104 via cable 110 can be communicated to conductor 142. Electrical energy communicated to conductor 142 is in turn communicated to collet 140 and/or electrode tip 116. The electrical connection between conductors 142, 144 can be maintained even when shaft 124 is moved between the retracted and extended positions. In particular, as shaft 124 is moved between the retracted and extended positions, sliding conductor 144 moves with shaft 124 and slides along conductor 142 to maintain the electrical connection therebetween. As a result electrical energy can be communicated from cable 110 to electrode tip 116 through the continuous connection between conductors 142, 144.

In some embodiments, sliding conductor 144 can be replaced with other electrical connections to hand piece 114. For instance, extendable shaft 124 may be electrically conductive and able to pass electrical current to electrode tip 116. For example, electrical energy can be communicated from cable 110 to conductor 142 and then from conductor 142 to electrically conductive shaft 124 and to electrode tip 116 (directly or through collet 140). In such embodiments, extendable shaft 124 may be formed from a conductive material that is at least partially coated with a non-conductive material to prevent the transfer of current from extendable shaft 124 to patient tissue during an electrosurgical procedure.

Alternatively, hand piece 114 and shaft 124 (or collet 140 or electrode tip 116) can be electrically connected with a flexible electrical ribbon to allows shaft 124 to move between the retracted and extended positions while maintaining electrical contact between hand piece 114 and shaft 124 (or collet 140 or electrode tip 116). In still other embodiments, cable 110 can extend into hand piece 114 and connect directly to shaft 124, conductor 144, collet 140, or electrode tip 116.

As shown, extendable shaft 124 can be formed with a length (measured along the proximal-distal axis) to be about the same length (e.g., within 99% of, 95% of, 90% of, 80% of, or 75%) of hand piece 114 in which it can selectively translate within. In other embodiments, extendable shaft 124 may be shorter or longer, such as about 0.75 times or 0.5 times the length of hand piece 114, or about 1.25, 1.5, 2, or 2.5 times longer than the length of hand piece 114.

As noted above and as can be seen in FIG. 4, extendable shaft 124 includes conduit 126 extending therethrough. Shaft 124 is configured to pass at least partially into interior conduit 136 of hand piece 114 such that conduit 126 is in fluid communication with conduit 136 and utility conduit 108 (and/or with vacuum hose 112 thereof). Extendable shaft 124 also includes a distal end opening 146 providing fluid communication between conduit 126 and the atmosphere exterior to extendable shaft 124. As shown, electrode tip 116 can be coupled to extendable shaft 124 (e.g., via collet 140 or other mechanisms (adhesive, welding, mechanical fastening, notches, slots, and/or friction fitting, or through integral formation of a single piece)) in a manner that leaves one or more aperture spaces for smoke capture into conduit 126 of extendable shaft 124.

Figure 5:
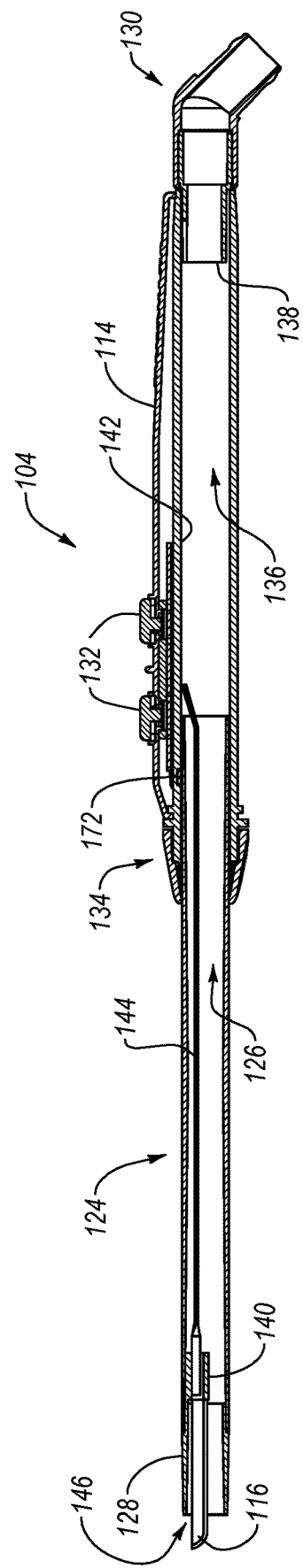
FIG. 5 illustrates a cross-sectional view of the electrosurgical instrument of FIGS. 2-4, showing the extendable shaft in the extended configuration.

FIG. 5 illustrates instrument 104 with extendable shaft 124 in an extended position. As can be seen, sliding conductor 144 remains in electrical contact with conductor 142 so that electrical energy can be communicated to electrode tip 116. Additionally, smoke or other fluids can be evacuated through conduits 126, 136 in shaft 124 and hand piece 114 and out through utility conduit 108 (or vacuum hose 112).

Attention is now directed to FIGS. 6-10, which illustrate locking mechanism 134 in greater detail. As noted above, locking mechanism 134 can selectively secure shaft 124 in a desired position relative to hand piece 114. For instance, locking mechanism 134 can selectively secure shaft 124 in the retracted position (see FIGS. 2 and 4), in the extended position (see FIGS. 3 and 5), or in one or more intermediate extended positions. Additionally, locking mechanism 134 can be selectively unlocked, disengaged, or loosened to enable shaft 124 to move between the retracted and extended positions.

Figure 6:
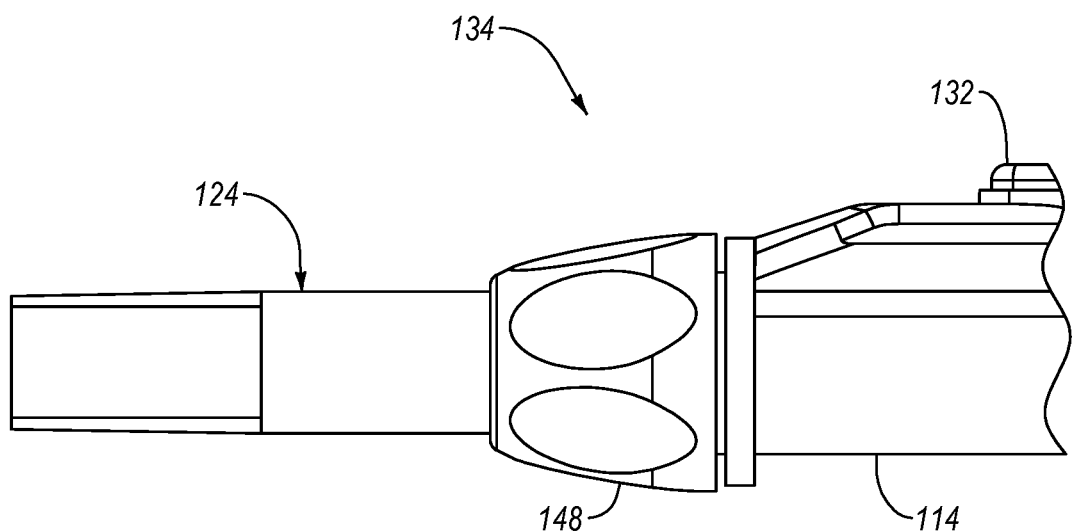
FIG. 6 illustrates the distal end of the electrosurgical instrument of FIGS. 2-5, showing a locking mechanism in a locked configuration.

FIG. 6 illustrates locking mechanism 134 in a locked, engaged, or tightened configuration. When locking mechanism 134 is in the locked, engaged, or tightened configuration, shaft 124 is secured in place relative to hand piece 114. In the illustrated embodiment, locking mechanism 134 is in the locked, engaged, or tightened configuration when a locking nut 148 is rotated (e.g., about shaft 124) so that locking nut 148 is moved proximally relative to hand piece 114.

Figure 7:
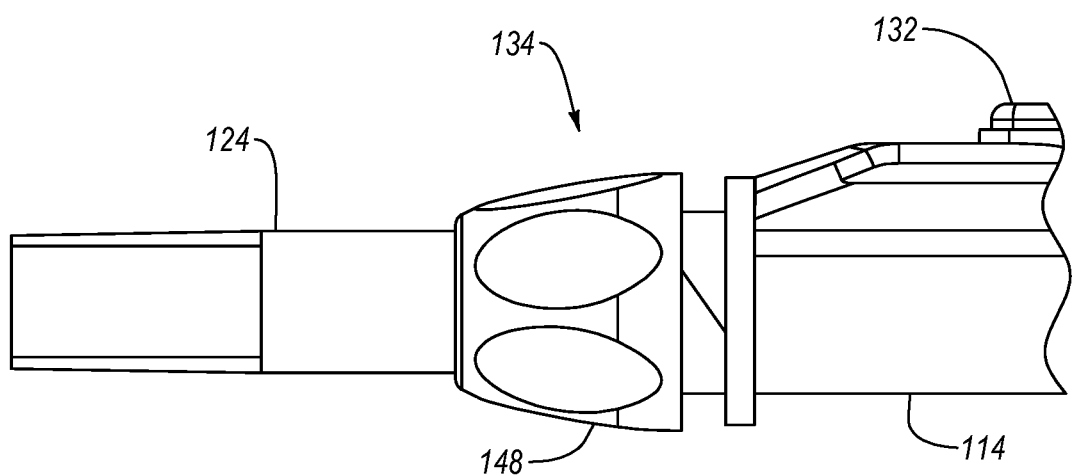
FIG. 7 illustrates the distal end of the electrosurgical instrument of FIGS. 2-5, showing the locking mechanism in an unlocked configuration.

In contrast, FIG. 7 illustrates locking mechanism 134 in an unlocked, disengaged, or loosened configuration. When locking mechanism 134 is in the unlocked, disengaged, or loosened configuration, shaft 124 is able to move relative to hand piece 114 between the retracted and extended positions. In the illustrated embodiment, locking mechanism 134 is in the unlocked, disengaged, or loosened configuration when locking nut 148 is rotated (e.g., about shaft 124) so that locking nut 148 is moved distally relative to hand piece 114.

Figure 8:
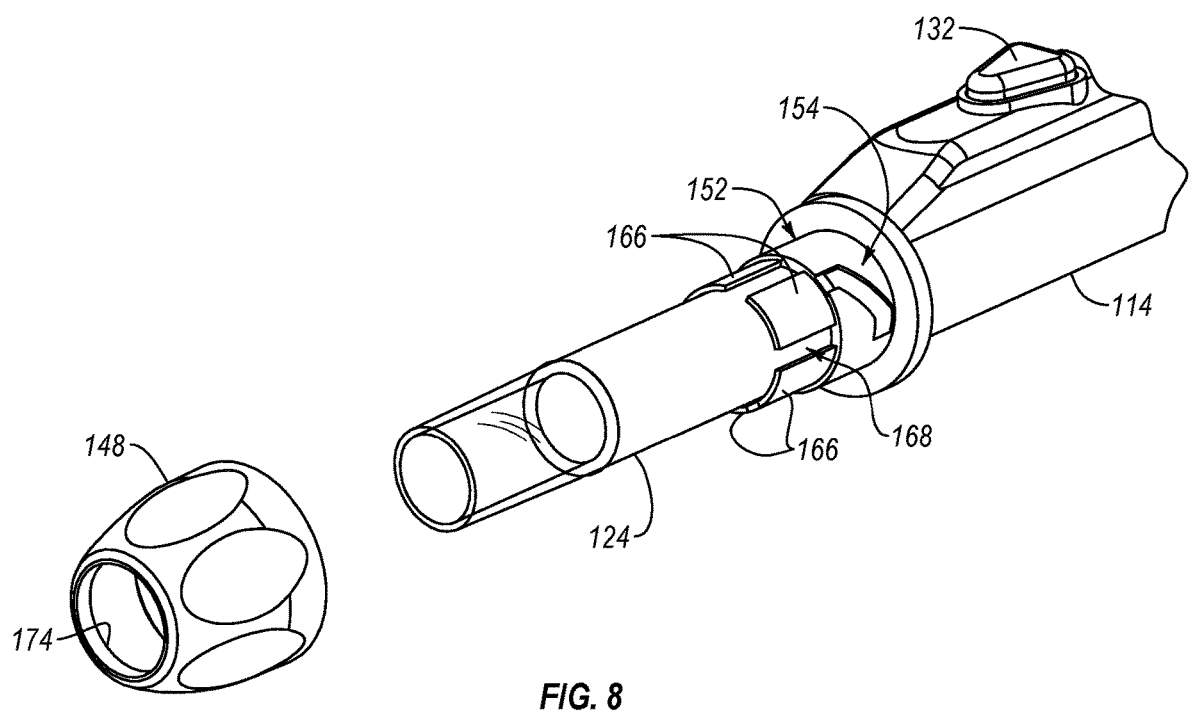
FIGS. 8-9 illustrate perspective views of the locking mechanism of FIGS. 6 and 7, with a locking nut disconnected.
Figure 9:
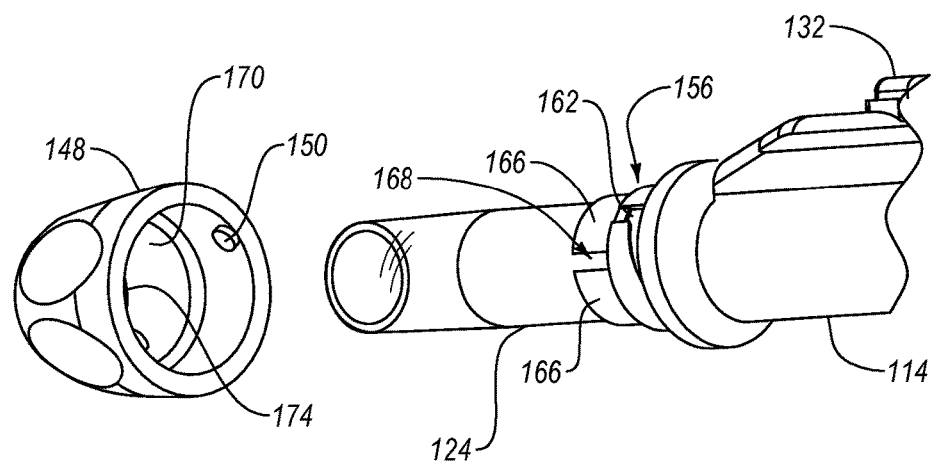

FIGS. 8-12 illustrate various views of locking mechanism 134. In particular, FIGS. 8 and 9 illustrate the distal end of instrument 104 with locking nut 148 disconnected from hand piece 114 to show interior features of locking mechanism 134. Similarly, FIGS. 10A-10B illustrate the distal end of instrument 104 with locking nut 148 disconnected from hand piece 114 and shown in shown in cross-section. FIGS. 11 and 12 show the distal end of instrument 104 in cross-section, with the locking mechanism 134 in the unlocked (FIG. 11) and locked (FIG. 12) configurations.

In the illustrated embodiment, locking nut 148 can slide over the distal end of shaft 124 (e.g., such that shaft 124 extends through locking nut 148) and can be secured or connected to hand piece 114. In general, the connection between locking nut 148 and hand piece 114 is achieved by way of mating pins and grooves, aspects of which are illustrated in FIGS. 8-10B. More specifically, locking nut 148 includes one or more engagement members, such as pins 150 (FIGS. 9-10A), spaced about its interior circumference. Pins 150 are configured and arranged to engage hand piece 114, as discussed below.

Figure 10A:
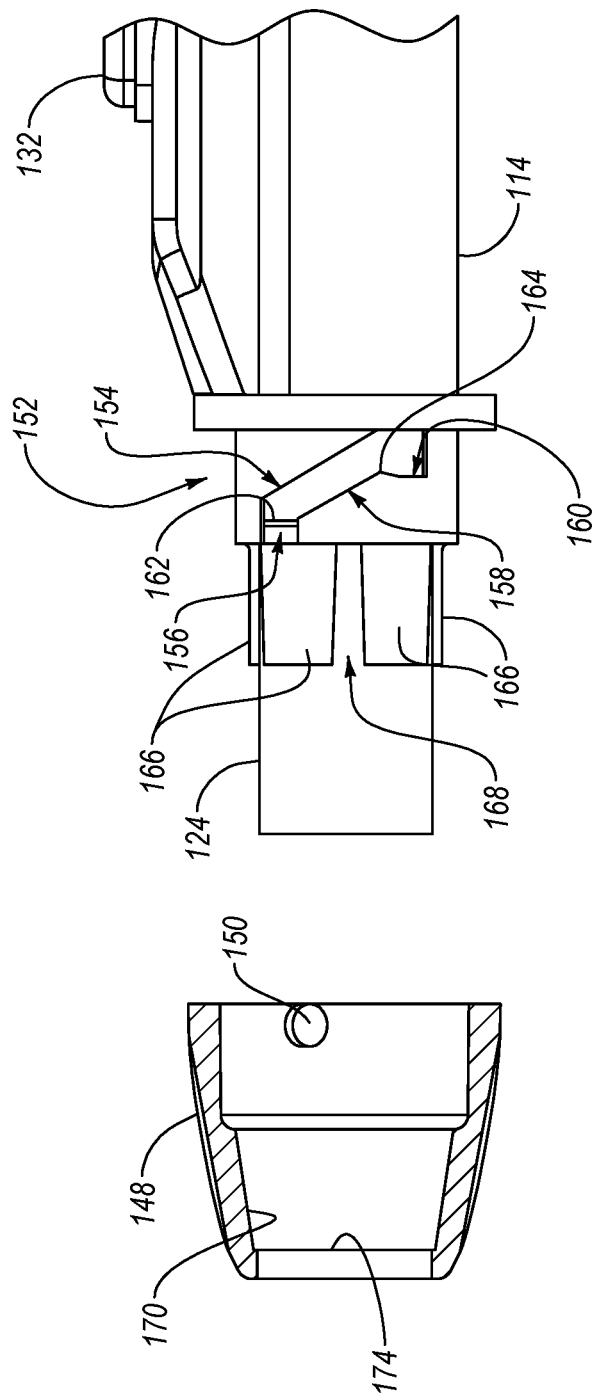
FIG. 10A illustrates a partial cross-sectional view of the locking mechanism showing the interior of the locking nut.

In correspondence with pins 150, hand piece 114 includes a collar 152 with one or more grooves 154 formed in an outer surface thereof. The grooves 154 can extend circumferentially around at least a portion of collar 152 and axially along at least a portion of the length of collar 152 (e.g., in the proximal/distal direction). The width and depth of grooves 154 generally correspond to the diameter and length, respectively, of pins 150. As best illustrated in FIG. 10A, each groove 154 includes three connected portions, or segments. Specifically, each groove 154 includes an entry segment 156, an intermediate segment 158, and a terminal segment 160. In some alternative embodiments, grooves 154 are defined by a structure that is discrete from, but attached or attachable to, hand piece 114.

In the illustrated embodiment, entry segment 156 extends proximally from a distal end of collar 152. In the illustrated embodiment, entry segment 156 is generally parallel with the proximal/distal axis of instrument 104. In other embodiments, entry segment 156 may extend axially along and circumferentially about collar 152.

In the illustrated embodiment, entry segment 156 also include a retention feature 162. Retention feature 162 may be configured to allow pin 150 to enter into groove 154 while restricting or preventing removal of pin 150 from groove 154. For instance, retention feature 162 may include an angled surface that allows pin 150 to slide over retention feature 162 as pin 150 is introduced into groove 154. Opposite the angled surface, retention feature 162 may include a retention wall that restricts or prevents pin 150 from being removed from groove 154.

Intermediate segment 158 is connected to entry segment 156 and extends proximally and circumferentially from entry segment 156. That is, intermediate segment 158 extends axially along and circumferentially about collar 152. As noted below, the angled orientation of intermediate segment 158 causes locking nut 148 to move axially relative to hand piece 114.

Terminal segment 160 is connected to intermediate segment 158. As can be seen in FIG. 10A, at least a portion of terminal segment 160 extends distally and in a direction generally parallel to the proximal/distal axis of instrument 104. In other embodiments, terminal segment 160 extends axially and circumferentially such that terminal segment 160 and intermediate segment 158 form an acute angle. In either case, a retention ridge 164 is formed between intermediate and terminal segments 158, 160. Retention ridge 164 is configured to selectively maintain pin 150 in terminal segment 160, thereby preventing locking nut 148 from being inadvertently loosened.

In general, the engagement of locking nut 148 and hand piece 114 is effected by positioning each pin 150 in a corresponding groove 154 and causing pins 150 to travel along or through grooves 154. More particularly, locking nut 148 and hand piece 114 are brought together until each pin 150 is positioned in the entry segment 156 of a corresponding groove 150 of hand piece 114. Locking nut 148 is then advanced proximally until pins 150 pass over retention features 162 in entry segments 156. When locking nut 148 is so positioned (e.g., with pins 150 in entry segments 156 proximal to retention feature 162), locking mechanism 134 is in the unlocked, disengaged, or loosened configuration as shown in FIG. 7.

Rotation of locking nut 148 (e.g., about shaft 124 or collar 152) is then initiated. As a result of the angular orientation of intermediate segments 158 with respect to a longitudinal (proximal/distal) axis of instrument 104, the rotation of locking nut 148 causes locking nut 148 to be drawn proximally towards hand piece 114. Continued rotation of locking nut 148 causes pins 150 to travel past retention ridges 164 and into the terminal segments 160. When locking nut 148 is rotated so pins 150 are positioned in terminal segments 160, locking mechanism 134 is in the locked, engaged, or tightened position as shown in FIG. 6.

To put the locking mechanism 134 in the unlocked, disengaged, or loosened position, locking nut 148 is moved proximally relative to hand piece 114 so as to allow pins 150 to pass over retention ridges 164. Locking nut 148 is then rotated so that pins 150 pass back through intermediate segments 158 and to entry segments 156. As will be appreciated, the angular configuration of intermediate segments 158 causes locking nut 148 to move distally relative to hand piece 114. As noted above, retention features 162 can also restrict or prevent pins 150 from exiting grooves 154, thereby restricting or preventing locking nut 148 from being completely disconnected from hand piece 114 when locking nut 148 is moved to the unlocked position.

It will be appreciated that the specific configuration and arrangement of the locking mechanism 134 and features thereof as shown in FIGS. 8-10A is illustrative only. For instance, FIG. 10B illustrates a locking mechanism 134A that includes elements that are similar to those of locking mechanism 134, but in a different configuration or arrangement. In particular, the position of the engagement members or pins and the grooves are reversed. Accordingly, instead of engagement members or pins being disposed on an interior surface a locking nut, the collar 152A includes one or more engagement members or pins 150A disposed on an exterior surface thereof. Similarly, instead of grooves being forming in an exterior surface of a collar, one or more grooves 154A are formed on an interior surface of locking nut 148A.

Figure 10B:
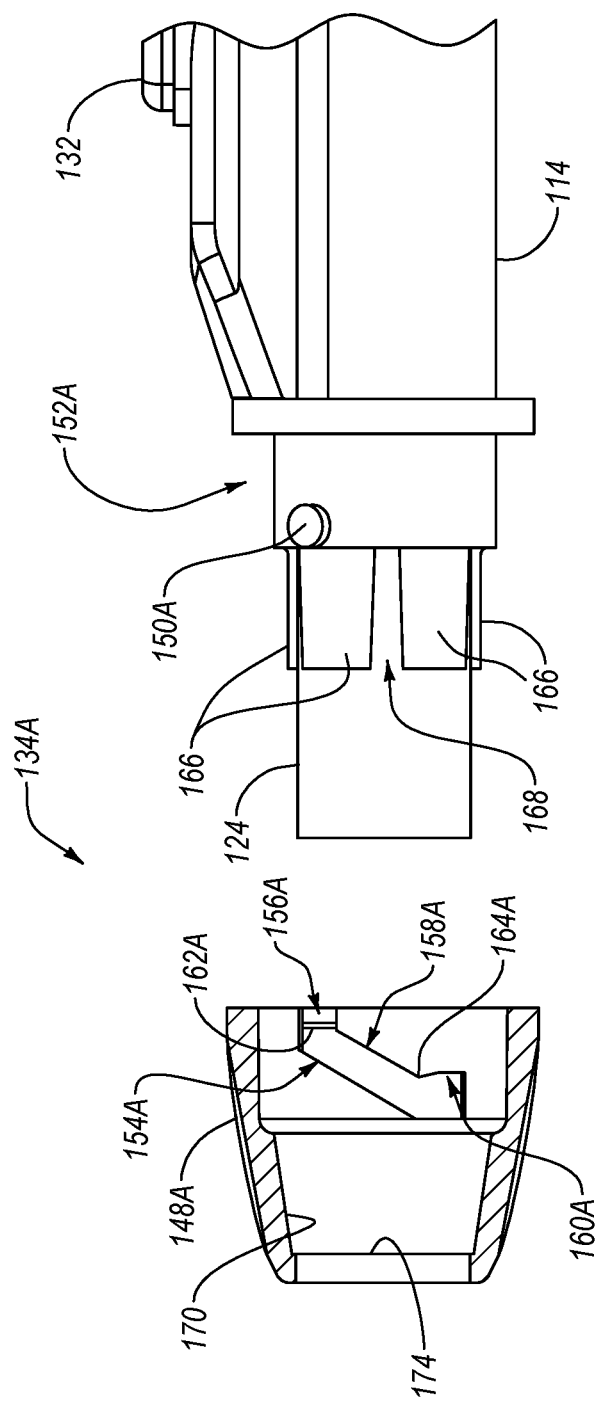

In the embodiment illustrated in FIG. 10B, locking nut 148A can slide over the distal end of shaft 124 (e.g., such that shaft 124 extends through locking nut 148A) and can be secured or connected to hand piece 114. In general, the connection between locking nut 148A and hand piece 114 is achieved by in a manner similar to that described above in connection with FIG. 10A. That is, the pins 150A can be inserted and advanced through the grooves 154A.

In contrast to groove 154 of FIG. 10A, groove 154A includes: (i) an entry segment 156A extends distally from a proximal end of locking nut 148A, (ii) an intermediate segment 158A connected to entry segment 156A and that extends distally and circumferentially from entry segment 156A, and (iii) a terminal segment 160A connected to intermediate segment 158A. As can be seen in FIG. 10B, at least a portion of terminal segment 160A extends proximally and in a direction generally parallel to the proximal/distal axis of instrument 104 such that a retention ridge 164A is formed between intermediate and terminal segments 158A, 160A.

In general, the engagement of locking nut 148A and hand piece 114 is effected by positioning each pin 150A in a corresponding groove 154A and causing pins 150A to travel along or through grooves 154A or grooves 154A to moves over pins 150a. More particularly, locking nut 148A and hand piece 114 are brought together until each pin 150A is positioned in the entry segment 156A of a corresponding groove 150A of in locking nut 148A. Locking nut 148 is then advanced proximally until pins 150 pass over retention feature 162A in entry segments 156A. When locking nut 148A is so positioned (e.g., with pins 150A in entry segments 156A distal to retention feature 162A), locking mechanism 134A is in the unlocked, disengaged, or loosened configuration as shown in FIG. 7.

Rotation of locking nut 148A (e.g., about shaft 124 or collar 152) is then initiated. As a result of the angular orientation of intermediate segments 158A with respect to a longitudinal (proximal/distal) axis of instrument 104, the rotation of locking nut 148A causes locking nut 148A to be drawn proximally towards hand piece 114. Continued rotation of locking nut 148A causes pins 150A to travel past retention ridges 164A and into the terminal segments 160A. When locking nut 148A is rotated so pins 150A are positioned in terminal segments 160A, locking mechanism 134A is in the locked, engaged, or tightened position as shown in FIG. 6.

To put the locking mechanism 134A in the unlocked, disengaged, or loosened position, locking nut 148A is moved proximally relative to hand piece 114 so as to allow pins 150A to pass over retention ridges 164A. Locking nut 148A is then rotated so that pins 150A pass back through intermediate segments 158A and to entry segments 156A. As will be appreciated, the angular configuration of intermediate segments 158A causes locking nut 148A to move distally relative to hand piece 114. As noted above, retention features 162A can also restrict or prevent pins 150A from exiting grooves 154A, thereby restricting or preventing locking nut 148A from being completely disconnected from hand piece 114 when locking nut 148A is moved to the unlocked position.

As the locking nut moves between the locked position (FIGS. 6 and 12) and the unlocked position (FIGS. 7 and 11), the locking nut interacts with compression flanges 166 to either secure shaft 124 in place or allow shaft 124 to move between the retracted and extended positions. As can be seen in FIGS. 8-10B, compression flanges 166 extend distally from collar 152 and are disposed circumferentially about shaft 124. Additionally, compression flanges 166 are spaced apart from one another such that a gap 168 is disposed between adjacent flanges 166. The gaps 168 between compression flanges 166 allow compression flanges 166 to be compressed or flexed inward towards shaft 124 as the locking nut moves from the unlocked position to the locked position.

As can be seen in FIGS. 9-12, locking nuts 148, 148A include a tapered interior surface 170. Surface 170 tapers in the distal direction such that surface 170 has a larger diameter at a proximal end than at a distal end. Tapered surface 170 interacts with compression flanges 166 to secure shaft 124 in place or to allow shaft 124 to move between the retracted and extended positions.

As can be seen in FIG. 11, when locking nut 148 is in the unlocked position (e.g., moved distally relative to hand piece 114 so that pins 150 are in or near the entry segments 156), the angled configuration of tapered surface 170 allows compression flanges 166 to flex away from shaft 124. As a result, the friction between compression flanges 166 and shaft 124 is reduced or eliminated, thereby allowing shaft 124 to move between the retracted and extended positions.

In contrast, as shown in FIG. 12, when locking nut 148 is moved to the locked position (e.g., moved proximally relative to hand piece 114 so that pins 150 are in or near the terminal segments 160), tapered surface 170 interacts with compression flanges 166 to flex or compress compression flanges 166 towards shaft 124. Tapered surface 170 can flex or compress compression flanges 166 against shaft 124 with sufficient force to secure shaft 124 in place. As a result, shaft 124 can be selectively maintained in a desired position (e.g., retracted, intermediate extended, or extended position).

As noted above, locking mechanism 134 can also prevent shaft 124 from being inadvertently removed from hand piece 114. For instance, shaft 124 and locking mechanism 134 can have cooperating features to limit the distal movement of shaft 124 relative to hand piece 114. In the illustrated embodiment, shaft 124 includes a stop 172 (FIGS. 4 and 5) on an exterior surface thereof adjacent to the proximal end of shaft 124. Stop 172 can interact with a shoulder 174 (FIGS. 8-12) on locking nut 148 to prevent shaft 124 from being (inadvertently) removed entirely from hand piece 114. By way of example, if locking mechanism 134 is moved to the unlocked configuration and shaft 124 is moved distally relative to hand piece 114, stop 172 will engage shoulder 174 prior to shaft 124 being removed entirely from hand piece 114. Thus, the interaction between stop 172 and shoulder 174 can prevent a surgeon or other personnel from inadvertently removing shaft 124 from hand piece 114 when attempting to adjust the extension of shaft 124 from hand piece 114.

Attention is now directed to FIG. 13, which illustrates a locking mechanism 134b. Locking mechanism 134b can be similar or identical to locking mechanism 134 and can be used with an electrosurgical instrument similar or identical to instrument 106 discussed above. For instance, locking mechanism 134b includes a collar 152b adjacent a distal end of a hand piece 114b. One or more grooves 154b may be disposed in collar 152b, similar or identical to grooves 154, for securing a locking nut (e.g., locking nut 148) to collar 152b in a similar manner as described above.

One distinction between locking mechanism 134b and locking mechanism 134 is that compression flanges 166b are not integrally formed with collar 152b or hand piece 114b. Rather, as illustrated in FIG. 13, compression flanges 166b (separated by gaps 168b) are connected to or integrally formed with a ring 180. Ring 180 is configured to be selectively connected to the distal end of collar 152b or hand piece 114b. Such connection can take a variety of forms. In the illustrated embodiment, for instance, ring 180 can be connected to collar 152b or hand piece 114b via a snap-fit connection. By way of example, an annular groove 182 is formed on an outer surface of the distal end of collar 152b or hand piece 114b. Ring 180 includes one or more corresponding detents 184 disposed on a proximal interior surface. Ring 180 can be connected to collar 152b or hand piece 114b by snapping detent(s) 184 into groove 182.

In some embodiments, ring 180 can provide a similar function as shoulder 174 described above. More specifically, ring 180 can prevent an extendable shaft (e.g., similar to shaft 124) from being inadvertently removed from hand piece 114b. As noted above in connection with shaft 124, an extendable shaft can include a stop (e.g., stop 172) on an exterior surface thereof. The stop can interact with ring 180 to prevent the shaft from being (inadvertently) removed entirely from hand piece 114b. By way of example, if locking mechanism 134b is moved to the unlocked configuration and an extendable shaft is moved distally relative to hand piece 114b, the stop will engage ring 180 prior to the shaft being removed entirely from hand piece 114b. Thus, the interaction between the stop and ring 180 can prevent a surgeon or other personnel from inadvertently removing the shaft from hand piece 114b when attempting to adjust the extension of the shaft from hand piece 114b.

Additionally, the ring 180 can be coupled to collar 152b or hand piece 114b so as to close off or block an open end of a track 186 formed on the interior of hand piece 114b. The track 186 may be configured to have the stop (e.g., stop 172) on the extendable shaft move therethrough as the extendable shaft is moved between extended and retracted positions. The open end of the track 186 shown in FIG. 13 may enable the stop to be inserted into the track 186, thereby allowing the extendable shaft to be inserted into the hand piece 114. Once the extendable shaft is inserted into the hand piece 114b and ring 18 is connect thereto, ring 180 can prevent the stop on the extendable shaft from exiting the end of the track 186. Retaining the stop in the track 186 can prevent undesirable rotation of the extendable shaft within hand piece 114b.

Attention is now directed to FIGS. 14-17 which illustrate another example of a locking mechanism according to the present disclosure. Rather than having compression flanges (e.g., 166, 166b) integrally formed with or connected to a collar (e.g., 152, 152b) or a hand piece (114, 114b), the illustrated embodiment includes compression flanges 166c integrally formed as part of or connected to a locking nut 148c. FIGS. 14 and 15 illustrate an end perspective view and a cross-sectional view of locking nut 148c. As can be seen, the compression flanges 166c extend proximally from an interior surface of locking nut 148c as are separated by gaps 168c.

When locking nut 148c is connected to collar 152c/hand piece 114c as shown in FIGS. 16 and 17, the compression flanges 166c extend proximally towards hand piece 114c. Additionally, the proximal ends of compression flanges 116c can extend into the distal end of collar 152c/hand piece 114c between the extendable shaft 124a and the distal end of collar 152c/hand piece 114c. When the locking nut 148c is in the locked position as shown in FIG. 16, the compression flanges extend deeper into collar 152c/hand piece 114c. As the compression flanges 166c extend deeper into collar 152c/hand piece 114c, the interior surface of collar 152c/hand piece 114c causes the compression flanges 166c to flex towards shaft 124a. As the compression flanges 166c flex towards shaft 124a, the friction between the compression flanges 166c and the shaft 124a increases sufficiently to secure the shaft 124a in place.

In contrast, when the locking nut 148c is in the unlocked position as shown in FIG. 17, the compression flanges are withdrawn at least partially from collar 152c/hand piece 114c. As the compression flanges 166c are withdrawn from collar 152c/hand piece 114c, the interior surface of collar 152c/hand piece 114c causes the compression flanges 166c to flex towards shaft 124a to a lesser degree compared to when the locking nut 148c is in the locked position. As a result, the friction between the compression flanges 166c and the shaft 124a is reduced sufficiently to allow the shaft 124a to move between the extended and retracted positions.

While the embodiments described herein have been directed to electrosurgical instruments with smoke evacuation features, the present disclosure is not intended to be so limited. Rather, the present disclosure is broadly directed to any instrument, hand-held or not, that includes an extendable shaft. The extendable shaft may increase the reach of the instrument and/or provide fluid evacuation or delivery capabilities. By way of non-limiting example, such instruments may include dental instruments (e.g., drills, polishing tools, scalers, compressed air tools, suction tools, irrigation tools, carries detection tools, water flossing tool (e.g., waterpik)), soldering tools (e.g., heated tools, smoke collection tools, de-soldering tools), high speed grinding and polishing tools (e.g., Dremel tools, carving tools, manicure tools, dental lab grinders/polishers), laser treatment instruments, laser surgical instruments, light probes, suction handles (e.g., Yankauer), blasting tools (e.g., sandblast, gritblast), shockwave therapy tools, ultrasonic therapy tools, ultrasonic probe tools, ultrasonic surgical tools, adhesive application instruments, glue guns, pneumatic pipettes, welding tools, RF wrinkle therapy devices, phaco devices, shears, shaver, or razor devices, micro drill devices, vacuum devices, small parts handling devices, tattoo needle handles, small torch devices, electrology devices, low speed grinding, polishing and carving tools, permanent makeup devices, electrical probe devices, ferromagnetic surgical devices, surgical plasma devices, argon beam surgical devices, surgical laser devices, surgical suction instruments (e.g., liposuction cannulas), surgical suction cannulas, microdermabrasion devices, fiberoptic cameras, microcamera devices, pH probe devices, fiberoptic and LED light source devices, hydrosurgery devices, orthopedic shaver, cutter, burr devices, wood burning tools, electric screwdrivers, electronic pad styluses, and the like.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An instrument, comprising:
    a body having a proximal end, a distal end, and an interior conduit defined by an interior surface, wherein a first portion of the interior surface has a first cross-sectional dimension along a length of the first portion of the interior surface, and wherein a second portion of the interior surface has a cross-sectional dimension that increases from the first cross-sectional dimension adjacent to the first portion to a second cross-sectional dimension closer to the distal end of the body, the second cross-sectional dimension being larger than the first cross-sectional dimension;
    an extendable shaft at least partially disposed within the interior conduit of the body and extending distally out of the distal end of the body, the extendable shaft having an outer dimension that generally corresponds to the first cross-sectional dimension of the interior surface of the interior conduit of the body such that the extendable shaft is selectively movable relative to the body between a retracted position and an extended position, wherein the increasing cross-sectional dimension of the interior surface creates a gap between a portion of the interior conduit and the extendable shaft, the gap having a dimension that decreases from a larger dimension adjacent to the distal end of the body to a smaller dimension adjacent the first portion of the interior surface; and
    a locking mechanism configured to selectively secure the extendable shaft in the retracted and extended positions, the locking mechanism comprising:
        one or more grooves associated with the body;
        a locking nut having one or more pins that are configured to travel through the one or more grooves to move the locking nut between a locked position and an unlocked position, the locking nut further comprising one or more compression flanges connected thereto or integrally formed therewith, the one or more compression flanges being configured to flex towards the extendable shaft when the locking nut is in the locked position and flex away from the extendable shaft when the locking nut is in the unlocked position, the one or more compression flanges being configured to restrict movement of the extendable shaft when the one or more compression flanges are flexed towards the extendable shaft, the one or more compression flanges being configured to extend proximally into the gap between the interior surface of the body and an exterior surface of the extendable shaft when the locking nut is moved to the locked position.

2. The instrument of claim 1, wherein the extendable shaft comprises a functional implement at a distal end thereof.

3. The instrument of claim 2, wherein the functional implement comprises an electrode tip, the electrode tip being configured to transmit electrical energy to a patient during an electro surgical procedure.

4. The instrument of claim 1, wherein the extendable shaft comprises a conduit extending therethrough.

5. The instrument of claim 1, wherein each of the one or more grooves comprises an entry segment, an intermediate segment, and a terminal segment.

6. The instrument of claim 5, wherein the entry segment extends in a direction parallel to an axis extending between the proximal and distal ends of the body.

7. The instrument of claim 6, wherein the entry segment comprises a retention feature configured to enable a pin of the one or more pins to enter the one or more grooves and prevent inadvertent removal of the pin from the one or more grooves.

8. The instrument of claim 7, wherein the retention feature comprises an angled surface that enables the pin to enter the one or more grooves and a retention wall that restricts movement of the pin out of the one or more grooves.

9. The instrument of claim 5, wherein the intermediate segment is angled such that the intermediate segment extends axially along and circumferentially around at least a portion of the body.

10. The instrument of claim 9, wherein the angled configuration of the intermediate segment causes the locking nut to move proximally or distally relative to the body as the one or more pins travel through the intermediate segments.

11. The instrument of claim 5, wherein the terminal segment extends from the intermediate segment in a direction towards the distal end of the body.

12. The instrument of claim 5, further comprising a retention ridge formed between the intermediate segment and the terminal segment, the retention ridge being configured to selectively retain the pin in the terminal segment.

13. The instrument of claim 1, wherein the body comprises a collar in which the one or more grooves are formed.

14. The instrument of claim 1, wherein the interior surface of the interior conduit comprises a tapered interior surface.

15. The instrument of claim 14, wherein the tapered interior surface is configured to interact with the one or more compression flanges to flex the compression flanges towards the extendable shaft when the locking nut is in the locked position.

16. The instrument of claim 1, wherein the extendable shaft comprises a stop adjacent a proximal end thereof.

17. The instrument of claim 16, wherein the locking nut further comprises a shoulder, wherein the stop on the extendable shaft and the shoulder are configured to interact to limit distal movement of the extendable shaft relative to the body.

18. An instrument, comprising:
a body having a proximal end, a distal end, and an interior conduit, the interior conduit comprising an interior surface, the interior surface having a first portion with a first cross-sectional dimension along a length thereof and a second portion with a cross-sectional dimension that increases from the first cross-sectional dimension adjacent to the first portion to a second cross-sectional dimension closer to the distal end of the body, the second cross-sectional dimension being larger than the first cross-sectional dimension;
a shaft selectively movable at least partially within the interior conduit and relative to the body between a retracted position and an extended position, the shaft having an outer dimension that generally corresponds to the first cross-sectional dimension of the interior surface of the interior conduit of the body, the shaft comprising a stop adjacent a proximal end thereof, the shaft and the second portion of the interior surface cooperating to form a gap therebetween, the gap having a dimension that decreases from a larger dimension adjacent to the distal end of the body to a smaller dimension adjacent the first portion of the interior surface; and
a locking mechanism configured to selectively secure the extendable shaft in the retracted and extended positions, the locking mechanism comprising:
a locking nut movably connected to and selectively retained on the body, the locking nut being selectively movable between a locked position and an unlocked position, the locking nut comprising one or more compression flanges connected thereto or integrally formed therewith, the one or more compression flanges being configured to extend proximally into the gap between the second portion of the interior surface of the body and the shaft and that are configured to flex towards and away from the shaft, movement of the locking nut from the unlocked position to the locked position being configured to move the one or more compression flanges proximally further into the gap between the second portion of the interior surface of the body and the shaft, the one or more compression flanges being configured to restrict movement of the shaft when the one or more compression flanges are flexed towards the shaft, the second portion of the interior surface being configured to flex the one or more compression flanges towards the shaft when the locking nut is moved to the locked position, the stop being configured to prevent complete removal of the shaft from the body.

19. The instrument of claim 18, wherein the one or more compression flanges are disposed circumferentially about the shaft.

20. An electrosurgical instrument, comprising:
a hand piece having a proximal end, a distal end, and an interior conduit defined by an interior surface, the interior surface comprising a first portion having a first cross-sectional dimension along a length of the first portion and a second portion having a cross-section dimension that increases from the first cross-sectional dimension adjacent to the first portion to a second cross-sectional dimension adjacent to the distal end of the hand piece;
a utility conduit connected to the hand piece, the utility conduit comprising a cable configured to communicate electrical energy to the electrosurgical instrument and a vacuum hose in fluid communication with the interior conduit;
a shaft disposed at least partially within the interior conduit of the hand piece and having an outer dimension that generally corresponds to the first cross-sectional dimension of the interior surface of the interior conduit of the hand piece such that the shaft is selectively extendable from the hand piece between a retracted position and an extended position, the shaft having a conduit therethrough that is in fluid communication with the interior conduit, an exterior surface of the shaft and the second portion of the interior surface of the interior conduit cooperating to form a gap between the interior conduit and the shaft, the gap having a dimension that decreases from a larger dimension adjacent to the distal end of the hand piece to a smaller dimension adjacent the first portion of the interior surface;
an electrode tip mounted in a distal end of the shaft, the electrode tip being configured to provide electrical energy to a target tissue; and
a locking mechanism configured to selectively secure the shaft in the retracted and extended positions, the locking mechanism comprising:
one or more grooves associated with the hand piece, each of the one or more grooves comprising an entry segment, an intermediate segment, and a terminal segment;
a locking nut comprising:
one or more pins that are configured to travel through the one or more grooves to move the locking nut between a locked position and an unlocked position; and
one or more compression flanges that are configured to flex towards the shaft when the locking nut is in the locked position and flex away from the shaft when the locking nut is in the unlocked position, the one or more compression flanges being configured to restrict movement of the shaft when the one or more compression flanges are flexed towards the shaft, wherein the one or more compression flanges are configured to extend proximally into the gap between the second portion of the interior surface of the hand piece and the exterior surface of the extendable shaft when the locking nut is moved from the unlocked position to the locked position;
one or more retention features that restrict removal of the one or more pins from the one or more grooves; and
one or more retention ridges that selectively maintain the one or more pins in the terminal segment of the one or more grooves.

* * * * *